United States Patent

Caparrelli

[11] Patent Number: 6,113,585
[45] Date of Patent: Sep. 5, 2000

[54] HAIR REMOVAL SYSTEM

[76] Inventor: Carla J. Caparrelli, 111 Scituate Ave., Johnston, R.I. 02919

[21] Appl. No.: 09/095,970

[22] Filed: Jun. 11, 1998

[51] Int. Cl.[7] .................................................. A61B 17/00
[52] U.S. Cl. ............................. 606/1; 606/131; 126/406
[58] Field of Search ................... 126/403–407, 126/409, 271.2 R; 431/344, 129; 606/1, 27–28, 131, 133

[56] References Cited

U.S. PATENT DOCUMENTS

| | | | |
|---|---|---|---|
| 196,711 | 10/1877 | Smeaton . | |
| 5,082,440 | 1/1992 | Yamamoto | 431/143 |
| 5,135,389 | 8/1992 | Dai et al. | 431/328 |
| 5,564,918 | 10/1996 | Lin | 431/255 |
| 5,769,701 | 6/1998 | Barber | 452/73 |
| 5,788,476 | 8/1998 | Sher | 431/153 |
| 5,915,955 | 6/1999 | Lin | 431/344 |

*Primary Examiner*—Linda C. M. Dvorak
*Assistant Examiner*—Roy Gibson

[57] ABSTRACT

A new hair removal system for removing hair from the body. The inventive device includes a housing having a perimeter side wall and a top surface. Extending from the top surface of the housing is a nozzle having an open terminal end. The nozzle is in fluid communication with the interior of the housing. A flame generating device is provided in the housing for generating a flame from the terminal end of the nozzle.

9 Claims, 2 Drawing Sheets

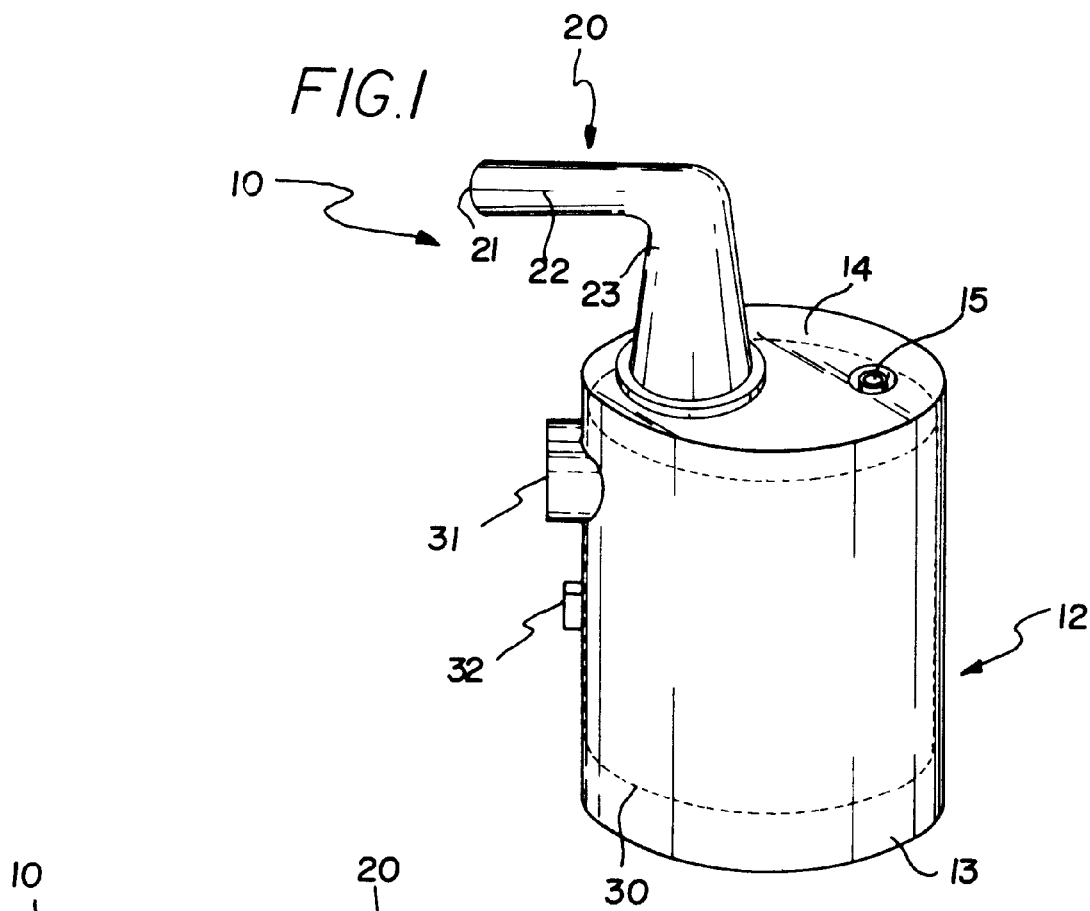
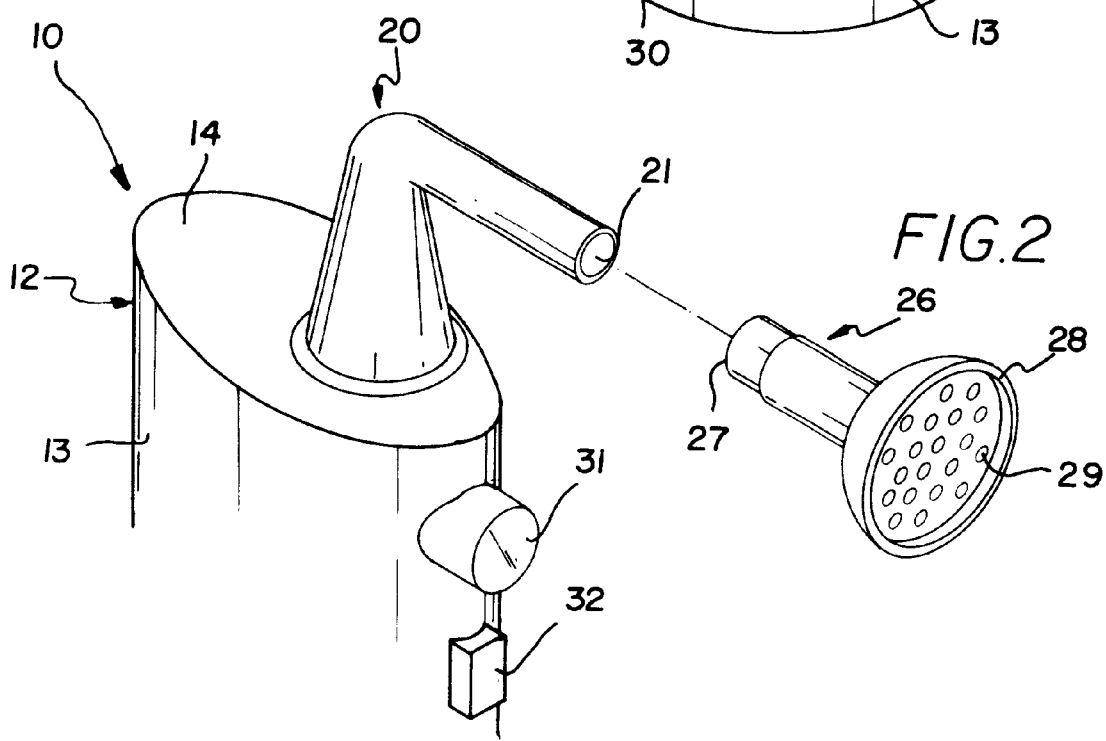

HAIR REMOVAL SYSTEM

BACKGROUND OF THE INVENTION

1. Field of the Invention

The present invention relates to hair removal devices and more particularly pertains to a new hair removal system for removing hair from the body.

2. Description of the Prior Art

The use of hair removal devices is known in the prior art. More specifically, hair removal devices heretofore devised and utilized are known to consist basically of familiar, expected and obvious structural configurations, notwithstanding the myriad of designs encompassed by the crowded prior art which have been developed for the fulfillment of countless objectives and requirements.

Known prior art hair removal devices include U.S. Pat. No. 3,955,913; U.S. Pat. No. 4,958,951; U.S. Pat. No. Des. 335,804; U.S. Pat. No. 5,084,046; U.S. Pat. No. 4,575,902; and U.S. Pat. No. Des. 285,897.

While these devices fulfill their respective, particular objectives and requirements, the aforementioned patents do not disclose a new hair removal system. The inventive device includes a housing having a perimeter side wall and a top surface. Extending from the top surface of the housing is a nozzle having an open terminal end. The nozzle is in fluid communication with the interior of the housing. A flame generating device is provided in the housing for generating a flame from the terminal end of the nozzle.

In these respects, the hair removal system according to the present invention substantially departs from the conventional concepts and designs of the prior art, and in so doing provides an apparatus primarily developed for the purpose of removing hair from the body.

SUMMARY OF THE INVENTION

In view of the foregoing disadvantages inherent in the known types of hair removal devices now present in the prior art, the present invention provides a new hair removal system construction wherein the same can be utilized for removing hair from the body.

The general purpose of the present invention, which will be described subsequently in greater detail, is to provide a new hair removal system apparatus and method which has many of the advantages of the hair removal devices mentioned heretofore and many novel features that result in a new hair removal system which is not anticipated, rendered obvious, suggested, or even implied by any of the prior art hair removal devices, either alone or in any combination thereof.

To attain this, the present invention generally comprises a housing having a perimeter side wall and a top surface. Extending from the top surface of the housing is a nozzle having an open terminal end. The nozzle is in fluid communication with the interior of the housing. A flame generating device is provided in the housing for generating a flame from the terminal end of the nozzle.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new hair removal system apparatus and method which has many of the advantages of the hair removal devices mentioned heretofore and many novel features that result in a new hair removal system which is not anticipated, rendered obvious, suggested, or even implied by any of the prior art hair removal devices, either alone or in any combination thereof.

It is another object of the present invention to provide a new hair removal system which may be easily and efficiently manufactured and marketed.

It is a further object of the present invention to provide a new hair removal system which is of a durable an(I reliable construction.

An even further object of the present invention is to provide a new hair removal system which is susceptible of a low cost of manufacture with regard to both materials and labor, and which accordingly is then susceptible of low prices of sale to the consuming public, thereby making such hair removal system economically available to the buying public.

Still yet another object of the present invention is to provide a new hair removal system which provides in the apparatuses and methods of the prior art some of the advantages thereof, while simultaneously overcoming some of the disadvantages normally associated therewith.

Still another object of the present invention is to provide a new hair removal system for removing hair from the body.

Yet another object of the present invention is to provide a new hair removal system which includes a housing having a perimeter side wall and a top surface. Extending from the top surface of the housing is a nozzle having an open terminal end. The nozzle is in fluid communication with the interior of the housing. A flame generating device is provided in the housing for generating a flame from the terminal end of the nozzle.

Still yet another object of the present invention is to provide a new hair removal system that burns or singes unwanted hair off of the body, especially hair on the face.

Even still another object of the present invention is to provide a new hair removal system that provides a smooth skin for a longer time than traditional hair removal devices.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a schematic perspective vies of a new hair removal system according to the present invention.

FIG. 2 is a schematic partial perspective view of the present invention illustrating the diffusing element.

DESCRIPTION OF THE PREFERRED EMBODIMENT

Figures 3, 4:
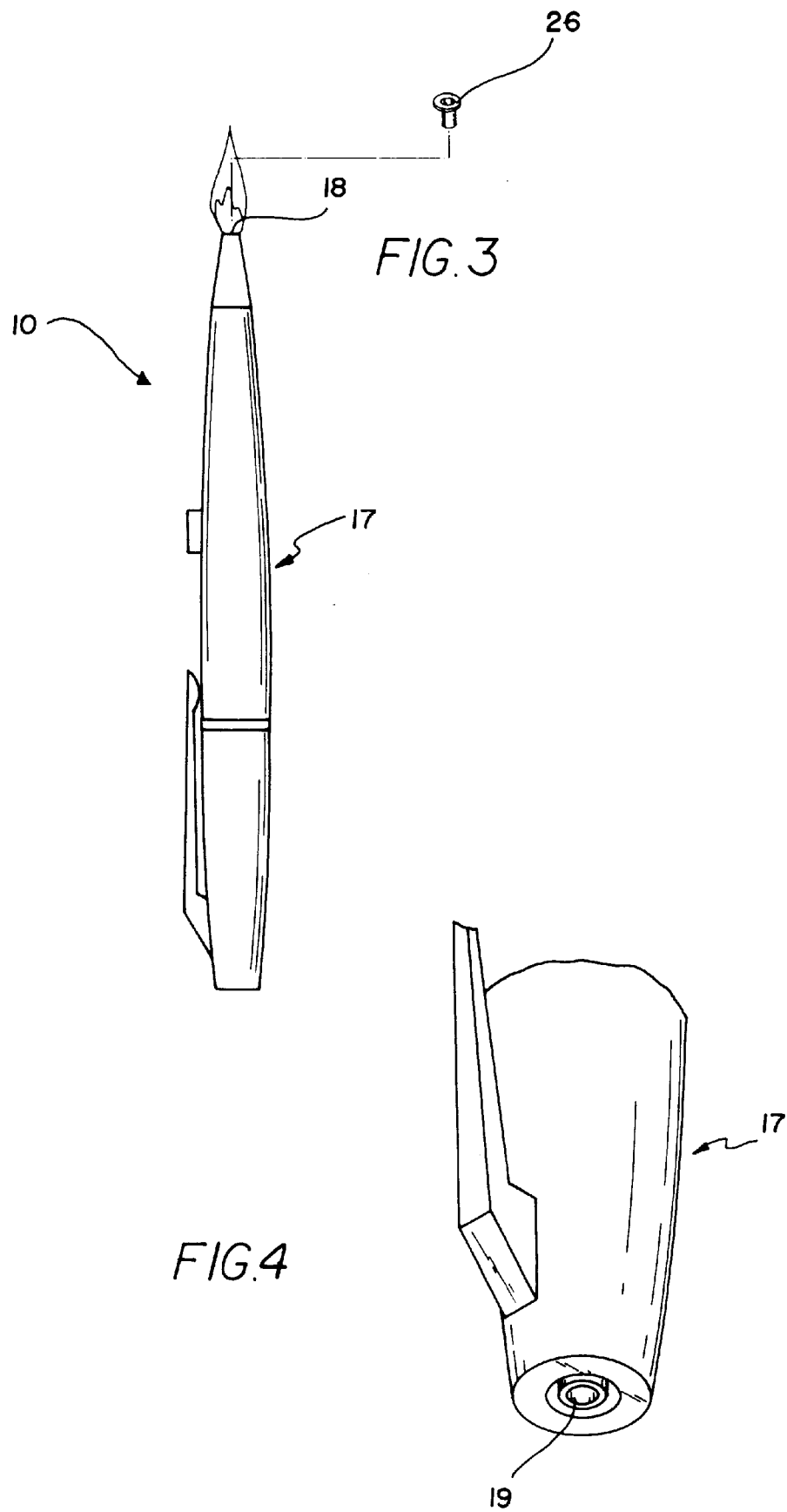
FIG. 3 is a schematic side view of the optional writing pen housing embodiment of the present invention.
FIG. 4 is a schematic partial perspective view of the optional writing pen housing embodiment of the present invention.

With reference now to the drawings, and in particular to FIGS. 1 through 4 thereof, a new hair removal system embodying the principles and concepts of the present invention and generally designated by the reference numeral 10 will be described.

As best illustrated in FIGS. 1 through 4, the hair removal device 10 generally comprises a housing 12 having a perimeter side wall 13 and a top surface 14. Extending from the top surface 14 of the housing 12 is a nozzle 20 having an open terminal end. The nozzle 20 is in fluid communication with the interior of the housing 12. A flame generating device 30 is provided in the housing 12 for generating a flame from the terminal end 21 of the nozzle 20.

In closer detail, as illustrated in FIGS. 1 and 2, the housing 12 is generally oblong with a generally oval and generally planar top surface 14 and a perimeter side wall 13. Ideally the housing is the size of a typical cigarette lighter. The nozzle 20 has an open terminal end and extends from the top surface 14 of the housing 12. The nozzle 20 is also in fluid communication with the interior of the housing 12. Preferably, the nozzle 20 is generally L-shaped with upper and lower portions 22,23. Ideally, the lower portion 23 of the nozzle 20 is extended in a plane generally perpendicular to the top face of the housing 12, and the upper portion 22 of the nozzle 20 is extended in a plane generally parallel to the plane of the top surface 14 of the housing 12.

The flame generating device 30 is provided in the housing 12. The flame generating device 30 generates a flame from the terminal end 21 of the nozzle 20 when activated. Preferably, the flame generating device 30 includes a first actuator 31 and a second safety actuator 32 provided on the side wall 13 of the housing 12. These actuator function similarly to the actuators of a cigarette lighter to prevent activation of the flame generating device 30 by a child by requiring activation (i.e., depression) of both actuators 31,32 to activate the flame generating device 30 to produce a flame. Ideally, butane fuel is used by the flame generating device 30 uses to generate a flame. In such an embodiment, it is preferred that the top surface 14 of the housing 12 has an opening 15 in fluid communication with the flame generating device 30 to permit refueling of the flame generating device 30.

As illustrated in FIG. 2, the diffusing element 26 has a hollow interior, an open insertion end 27 and a flared diffusion end 28. The insertion end 27 of the diffusing element 26 is detachably inserted into the open terminal end 21 of the nozzle 20 such that the diffusing element 26 is in fluid communication with a flame generated by the flame generating device 30. The diffusion end 28 of the diffusing element has a plurality of openings 29 into the hollow interior of the diffusing element 26. The openings 29 of the diffusion end 28 are designed for diffusing a flame emitted from the open terminal end 21 of the nozzle 20.

In an optional embodiment, as illustrated in FIGS. 3 and 4, the housing is shaped to generally resemble a writing pen 17 with an open tip 18. The flame generating device 30 generates a flame from the open top 18 of the writing pen shaped housing 17 when activated. As illustrated in FIG. 4, the writing pen shaped housing 12 may also include an opening 19 in fluid communication with the flame generating device 30 to permit refueling of the flame generating device 30. In this optional embodiment, the diffusing element may be inserted into the open tip 18.

In use, the hair removal device 10 is used to remove hair from the body, especially unwanted facial hair. The flame generating device 30 is activated to generate a flame emitting from the terminal end 21 of the nozzle 20. The open terminal end 21 of the nozzle 20 is then positioned adjacent a hair on a body so that the hair may be burned off by the flame emitting from the open terminal end 21 of the nozzle 20. When the diffusing element 26 is included on the device 10, the diffusion end 28 of the diffuser element is positioned adjacent a hair on a body so that the hair can be burned off.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A hair removal device, comprising:
   a housing having an interior, a perimeter side wall and a top surface;
   a nozzle having an open terminal end, said nozzle being extended from said top surface of said housing, said nozzle being in fluid communication with said interior of said housing, a flame generating device being provided in said housing, said flame generating device generating a flame from said terminal end of said nozzle; and a diffusing element having a hollow interior, an open insertion end and a flared diffusion end, said insertion end of said diffusing element being detachably inserted into said open terminal end of said nozzle such that said diffusing element is in fluid communication with a flame generated by said flame generating device, said diffusion end of said diffusing element having a plurality of openings into said hollow interior of said diffusing element, said openings of said diffusion end being for diffusing a flame emitted from said open terminal end of said nozzle.

2. The device of claim 1, wherein said housing is generally oblong and has a generally oval and generally planar top surface.

3. The device of claim 1, wherein said housing is shaped to generally resemble a writing pen having an open tip, said flame generating device generating a flame from said open top of said writing pen shaped housing when activated, said writing pen shaped housing having an opening in fluid communication with said flame generating device to permit refueling of said flame generating device.

4. The device of claim 1, wherein said nozzle is generally L-shaped and having upper and lower portions, said lower portion of said nozzle being extended in a plane generally perpendicular to said top face of said housing, said upper portion of said nozzle being extended in a plane generally parallel to the plane of said top surface of said housing.

5. The device of claim 1, wherein said flame generating device includes first and second actuators being provided on said side wall of said housing, wherein activation of both of said actuators activates said flame generating device to produce a flame.

6. The device of claim 1, wherein said top surface of said housing has an opening in fluid communication with said flame generating device to permit refueling of said flame generating device.

7. A hair removal device, comprising:

a housing being generally oblong and having an interior, a perimeter side wall and a generally oval and generally planar top surface;

a nozzle having an open terminal end, said nozzle being generally L-shaped and having upper and lower portions, said nozzle being extended from said top surface of said housing, said lower portion of said nozzle being extended in a plane generally perpendicular to said top face of said housing, said upper portion of said nozzle being extended in a plane generally parallel to the plane of said top surface of said housing, said nozzle being in fluid communication with said interior of said housing, a flame generating device being provided in said housing, said flame generating device generating a flame from said terminal end of said nozzle, wherein butane fuel is used by said flame generating device uses to generate a flame, said flame generating device including first and second actuators being provided on said side wall of said housing, wherein activation of both of said actuators activating said flame generating device to produce a flame;

said top surface of said housing having an opening in fluid communication with said flame generating device to permit refueling of said flame generating device; and a diffusing element having a hollow interior, an open insertion end and a flared diffusion end, said insertion end of said diffusing element being detachably inserted into said open terminal end of said nozzle such that said diffusing element is in fluid communication with a flame generated by said flame generating device, said diffusion end of said diffusing element having a plurality of openings into said hollow interior of said diffusing element, said openings of said diffusion end being for diffusing a flame emitted from said open terminal end of said nozzle.

8. A method for removing hair from a body, comprising the steps of:

providing hair removal device comprising:

a housing having an interior, a perimeter side wall and a top surface;

a nozzle having an open terminal end, said nozzle being extended from said top surface of said housing, said nozzle being in fluid communication with said interior of said housing, and a flame generating device being provided in said housing, said flame generating device generating a flame from said terminal end of said nozzle;

activating said flame generating device to generate a flame emitting from said terminal end of said nozzle;

positioning said open terminal end of said nozzle adjacent a hair on a body; and burning said hair by said flame emitting from said open terminal end of said nozzle.

9. The method of claim 8, further comprising the steps of providing a diffusing element having a hollow interior, an open insertion end and a flared diffusion end, said insertion end of said diffusing element being detachably inserted into said open terminal end of said nozzle such that said diffusing element is in fluid communication with a flame generated by said flame generating device, said diffusion end of said diffusing element having a plurality of openings into said hollow interior of said diffusing element; and positioning said diffusion end of said diffuser element adjacent a hair on a body.

* * * * *